(12) United States Patent
Fan et al.

(10) Patent No.: US 7,444,045 B2
(45) Date of Patent: Oct. 28, 2008

(54) HYBRID SPHERE-WAVEGUIDE RESONATORS

(75) Inventors: Xudong Fan, Austin, TX (US); John E. Potts, Woodbury, MN (US); Terry L. Smith, Roseville, MN (US); Robert W. Wilson, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 674 days.

(21) Appl. No.: 10/685,049

(22) Filed: Oct. 14, 2003

(65) Prior Publication Data

US 2005/0077513 A1 Apr. 14, 2005

(51) Int. Cl.
*G02B 6/26* (2006.01)
(52) U.S. Cl. .............................. 385/27; 385/30; 385/31; 385/39; 385/42; 385/43; 385/50; 385/51; 385/52; 385/123; 385/129; 385/130; 385/132
(58) Field of Classification Search ................. 385/27, 385/30–31, 39, 42–43, 50–52, 123, 129–130, 385/132
See application file for complete search history.

(56) References Cited

U.S. PATENT DOCUMENTS

| | | | |
|---|---|---|---|
| 3,833,284 A | 9/1974 | Kaminow et al. | |
| 4,715,672 A | 12/1987 | Duguay et al. | |
| 4,978,187 A | 12/1990 | Minemura et al. | |
| 5,077,822 A | 12/1991 | Cremer | |
| 5,214,664 A | 5/1993 | Paoli | |
| 6,219,361 B1 | 4/2001 | Guch, Jr. et al. | |
| 6,389,197 B1 | 5/2002 | Iltchenko et al. | |
| 6,490,039 B2 | 12/2002 | Maleki et al. | |
| 6,507,684 B2 | 1/2003 | Tapalian et al. | |
| 6,512,866 B1 | 1/2003 | Fan et al. | |
| 6,583,399 B1 | 6/2003 | Hunziker et al. | |
| 6,594,425 B2 | 7/2003 | Tapalian et al. | |
| 6,657,731 B2 | 12/2003 | Tapalian et al. | |
| 6,665,476 B2 | 12/2003 | Braun et al. | |
| 6,668,111 B2 | 12/2003 | Tapalian et al. | |
| 6,777,244 B2 | 8/2004 | Pepper et al. | |

(Continued)

FOREIGN PATENT DOCUMENTS

GB 2 293 883 4/1996

(Continued)

OTHER PUBLICATIONS

Johnson, B.R.; "Theory of Morphology-Dependent Resonances: Shape Resonances and Width Formulas", *J. Opt. Soc. Am. A* (Feb. 1993); vol. 10, No. 2; pp. 343-352.

(Continued)

*Primary Examiner*—Frank G Font
*Assistant Examiner*—Michael P Mooney
(74) *Attorney, Agent, or Firm*—Robert S. Moshrefzadeh

(57) ABSTRACT

Microresonators, such as a microsphere resonators and planar microresonators, are optically coupled to waveguides for input and output of light. It is important that the relative positions of the microresonator and the waveguide are maintained stable, while still maintaining high cavity Q and ease of launching and extracting the optical beams. Structures are provided on a substrate that are useful for maintaining the position of the microresonator relative to the waveguide. The structures provide for vertical or horizontal coupling between the waveguide and the microresonator.

38 Claims, 13 Drawing Sheets

U.S. PATENT DOCUMENTS

| | | | |
|---|---|---|---|
| 6,781,696 B1 | 8/2004 | Rosenberger et al. | |
| 6,795,481 B2 | 9/2004 | Maleki et al. | |
| 6,813,285 B2 | 11/2004 | Peterson | |
| 6,853,479 B1 | 2/2005 | Ilchenko et al. | |
| 6,865,317 B2 | 3/2005 | Vahala et al. | |
| 6,879,752 B1 | 4/2005 | Ilchenko et al. | |
| 6,888,987 B2 | 5/2005 | Sercel et al. | |
| 6,891,996 B2 | 5/2005 | Sercel et al. | |
| 6,891,997 B2 | 5/2005 | Sercel et al. | |
| 6,895,135 B2 | 5/2005 | Kaneko et al. | |
| 6,901,101 B2 * | 5/2005 | Frick | 372/92 |
| 7,091,049 B2 | 8/2006 | Boga et al. | |
| 2001/0038651 A1 | 11/2001 | Maleki et al. | |
| 2002/0018611 A1 | 2/2002 | Maleki et al. | |
| 2002/0041730 A1 | 4/2002 | Sercel et al. | |
| 2002/0044739 A1 * | 4/2002 | Vahala et al. | 385/30 |
| 2002/0068018 A1 | 6/2002 | Pepper et al. | |
| 2002/0079453 A1 | 6/2002 | Tapalian et al. | |
| 2002/0094150 A1 | 7/2002 | Lim et al. | |
| 2002/0097401 A1 | 7/2002 | Maleki et al. | |
| 2002/0172457 A1 | 11/2002 | Tapalian et al. | |
| 2002/0192680 A1 | 12/2002 | Chan et al. | |
| 2003/0016907 A1 | 1/2003 | LoCascio et al. | |
| 2003/0082237 A1 | 5/2003 | Cha et al. | |
| 2004/0023396 A1 | 2/2004 | Boyd et al. | |
| 2004/0091212 A1 | 5/2004 | Strecker et al. | |
| 2004/0120638 A1 | 6/2004 | Frick | |
| 2004/0146431 A1 | 7/2004 | Scherer et al. | |
| 2004/0196465 A1 | 10/2004 | Arnold et al. | |
| 2005/0035278 A1 | 2/2005 | Margalit et al. | |
| 2005/0078731 A1 | 4/2005 | Fan et al. | |
| 2005/0105868 A1 | 5/2005 | Arakida | |
| 2005/0111309 A1 | 5/2005 | Peng | |
| 2005/0147372 A1 | 7/2005 | Bourdelais et al. | |
| 2005/0249509 A1 | 11/2005 | Nagarajan et al. | |
| 2005/0263679 A1 | 12/2005 | Fan et al. | |
| 2005/0265658 A1 | 12/2005 | Fan et al. | |
| 2006/0110100 A1 | 5/2006 | Blauvelt et al. | |
| 2006/0170931 A1 | 8/2006 | Guo et al. | |

FOREIGN PATENT DOCUMENTS

| | | |
|---|---|---|
| GB | 2 387 130 | 10/2003 |
| WO | WO 01/40757 A2 | 6/2001 |
| WO | WO 01/67565 | 9/2001 |
| WO | WO 01/85341 | 11/2001 |
| WO | WO 02/13337 | 2/2002 |
| WO | WO 02/16986 | 2/2002 |
| WO | WO 2004/038370 A2 | 5/2004 |

OTHER PUBLICATIONS

Little, B.E., et al; "Pedestal Antiresonant Reflecting Waveguides for Robust Coupling to Microsphere Resonators and for Microphotonic Circuits", *Optics Letters* (Jan. 1, 2000); vol. 25, No. 1; pp. 73-75.

Laine, J.-P., et al; "Microsphere Resonator Mode Characterization by Pedestal Anti-Resonant Reflecting Waveguide Coupler", *IEEE Photonics Technology Letters* (Aug. 2000); vol. 12, No. 8; pp. 1004-1006.

Burlak, G., et al; "Electromagnetic Osciliations in a Multilayer Spherical Stack", *Optics Communications*, (Jun. 1, 2000); vol. 180; Elsevier Science B.V.; pp. 49-58.

Laine, J.-P., et al; "Acceleration Sensor Based on High-Q Optical Microsphere Resonator and Pedestal Antiresonant Reflecting Waveguide Coupler", *Sensors and Actuators A* (2001); vol. 93; Elsevier Science B.V.; pp. 1-7.

Chan, S., et al; "Identification of Gram Negative Bacteria Using Nanoscale Silicon Microcavities", Communications to the Editor, *Journal of American Chemical Society* (Nov. 2001); vol. 123, pp. 11797-11798.

Burlak, G., et al; "Electromagnetic Eigenoscillations and Fields in a Dielectric Microsphere with Multilayer Spherical Stack", *Optics Communications* (Jan. 1, 2001); vol. 187, Elsevier Science B.V.; pp. 91-105.

Chan, S., et al; "Nanoscale Silicon Microcavities for Biosensing", *Materials Science and Engineering C* (2001); vol. 15, Elsevier Science B.V.; pp. 277-282.

Spillane, S.M., et al; "Ultralow-Threshold Raman Laser Using a Spherical Dielectric Microcavity", Letters to Nature, *Nature* (Feb. 7, 2002); vol. 415, Macmillan Magazines Ltd.; pp. 621-623.

Lugo, J.E., et al; "Porous Silicon Multilayer Structures: A Photonic Band Gap Analysis", *Journal of Applied Physics* (Apr. 15, 2002); vol. 91, No. 8; pp. 4966-4972.

Burlak, G., et al; "Transmittance and Resonance Tunneling of the Optical Fields in the Microspherical Metal-Dielectric Structures", *Optics Communications* (May 15, 2002); vol. 206, Elsevier Science B.V.; pp. 27-37.

Vollmer, F., et al; "Protein Detection by Optical Shift of a Resonant Microcavity", *Applied Physics Letters* (May 27, 2002); vol. 80, No. 21; pp. 4057-4059.

Krioukov, E., et al; "Integrated Optical Microcavities for Enhanced Evanescent-Wave Spectroscopy", *Optics Letters* (Sep. 1, 2002); vol. 27, No. 17; pp. 1504-1506.

Armani, D.K., et al; "Ultra-High-Q Toroid Microcavity on a Chip", Letters to Nature, *Nature* (Feb. 27, 2003); vol. 421, Nature Publishing Group; pp. 925-928.

Tapalian, C., et al; "High-Q Silica Microsphere Optical Resonator Sensors Using Stripline-Pedestal Anti-Resonant Reflecting Optical Waveguide Couplers"; *Proceedings from SPIE, Photonics West 2003* (Jan. 25-31, 2003); vol. 4969; Laser Resonators and Beam Control VI; Item 4969-30; pp. 11-22.

U.S. Appl. No. 10/685,208, filed Oct. 14, 2003, Porous Microsphere Resonators.

Knight, J.C., et al; "Mapping Whispering-Gallery Modes in Microspheres with a Near-Field Probe", *Optics Letters* (Jul. 15, 1995); vol. 20, No. 14; pp. 1515-1517.

Kakarantzas, G., et al; "Miniature All-Fiber Devices Based on $CO_2$ Laser Microstructuring of Tapered Fibers", *Optics Letters* (Aug. 1, 2001); vol. 26, No. 15; pp. 1137-1139.

Boyd et al., "Sensitive disk resonator photonic biosensor", Applied Optics, vol. 40, No. 31, Nov. 1, 2001, pp. 5742-5747.

Krioukov et al., "Sensor based on an integrated optical microcavity", Optics Letters, vol. 27, No. 7, Apr. 1, 2002, pp. 512-514.

Blair et al., "Resonant-enhanced evanescent-wave fluorescence biosensing with cylindrical optical cavities", Applied Optics, vol. 40, No. 4, Feb. 1, 2001, pp. 570-582.

Yunfeng et al., "Chemical sensors based on hydrophobic porous sol-gel films and ATR-FTIR spectroscopy", Sensors and Actuators B, Elsevier Sequoia S.A., vol. B36, No. 1, 2, and 3, Oct. 1996, pp. 517-521.

Crisan et al., "Sol-Gel Preparation of Thin Films for Integrated Optics", 10th International Symposium on Electron Devices for Microwave and Optoelectronic Applications, Nov. 18-19, 2002, Manchester, UK., pp. 205-210.

Coffer et al., "Strategies Toward the Development of Integrated Chemical Sensors Fabricated from Light Emitting Porous Silicon", Proceedings of the SPIE, vol. 3226, 1997, pp. 168-179.

Shibata et al., "Laser Emission from Dye-Doped Organic-Inorganic Particles of Mircocavity Structure", Journal of Sol-Gel Science and Technology, vol. 8, 1997, pp. 959-964.

Wark et al., "Incorporation of organic dye molecules in nanoporous crystals for the development of hexagonal solid state microlasers", Proceedings of the SPIE, vol. 4456, 2001, pp. 57-67.

Pipino et al., "Evanescent wave cavity ring-down spectroscopy with a total-internal-reflection minicavity", Review of Scientific Instruments, American Institute of Physics, vol. 68, No. 8, Aug. 8, 1997, pp. 2978-2989.

Luk, J.M.C., et al; "Rapid and Sensitive Detection of *Salmonella* (O : 6,7) by Immunomagnetic Monoclonal Antibody-Based Assays", *Journal of Immunological Methods* (1991); vol. 137; pp. 1-8.

Martin, A.L., et al; "Replica-Molded High-Q Polymer Microresonators", *Optics Letters* (Mar. 15, 2004); vol. 29, No. 6; pp. 533-535.

Pettipher, G.L., et al; "Rapid Enumeration of Microorganisms in Foods by the Direct Epifluorescent Filter Technique", *Applied and Environmental Microbiology* (Oct. 1982); vol. 44, No. 4; pp. 809-813.

Plowman, T.E., et al; "Femtomolar Sensitivity Using a Channel-Etched Thin Film Waveguide Fluoroimmunosensor", *Biosensors & Bioelectronics* (1996); Elsevier Science Ltd.; vol. 11, No. 1/2; pp. 149-160.

Popescu, A., et al; "The Gram Stain after More than a Century", *Biotechnic and Histochemistry* (1996); vol. 71, No. 3; pp. 145-151.

Sumetsky, M., "Whispering-Gallery-Bottle Microcavities: the Three-Dimensional Etalon", *Optics Letters* (Jan. 1, 2004); vol. 29, No. 1; pp. 8-10.

Tortorello, M.L., et al; "Antibody-Direct Epifluorescent Filter Technique for Rapid, Direct Enumeration of *Escherichia coli* O157:H7 in Beef", *Applied and Environmental Microbiology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Vernooy, D.W., et al; "High-Q Measurements of Fused-Silica Microspheres in the Near Infrared", *Optics Letters* (Feb. 15, 1998); vol. 23, No. 4; pp. 247-249.

Xu, G.; "Gram Stain", University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.htm>; pp. 10.

Garmire, E., et al., "Propagation Losses in Metal-Film-Substrate Optical Waveguides," *Journal of Quantum Electronics*, vol. QE-8, No. 10, Oct. 1972, pp. 763-766.

Kaminow, I.P., et al., "Metal-Clad Optical Waveguides: Analytical and Experimental Study," *Applied Optics*, vol. 13, No. 2, Feb. 1974, pp. 396-405.

Otto, A., et al., "Modification of the Total Reflection Modes in a Dielectric Film by One Metal Boundary," *Optics Communications*, vol. 3, No. 4, Jun. 1971, pp. 254-258.

Reisinger, A., "Attenuation Properties of Optical Waveguides with a Metal Boundary," *Appl. Phys. Lett.*, vol. 23, No. 5, Sep. 1, 1973, pp. 237-239.

Suematsu, et al., "Fundamental Transverse Electric Field ($TE_0$) Mode Selection for Thin-Film Asymmetric Light Guides," *Appl. Phys. Lett.*, vol. 21, No. 6, Sep. 15, 1972, pp. 291-293.

Tien, P., et al., "Novel Metal-clad Optical Components and Method of Isolating High-Index Substrates for Forming Integrated Optical Circuits," *Appl. Phys. Lett.*, vol. 27, No. 4, Aug. 15, 1975, pp. 251-253.

Yoneyama et al., "Nonradiative Dielectric Waveguide Circuit Components" *International Journal of Infrared and Millimeter Waves*, vol. 4, No. 3, (1983), pp. 439-449.

Chan, S., et al. "Porous Silicon Microcavities for Biosensing Applications," *Physical Status Solid*, vol. 182, (2000) pp. 541-546.

De Stefano, L., et al., "Optical Sensing of Flammable Substances Using Porous Silicon Microcavities," *Materials Science and Engineering*, vol. 100, Jul. 25, 2003, pp. 271-274.

Mulloni, V., et al. "Porous Silicon Microcavities. as Optical Chemical Sensors," *Applied Physics Letters*, vol. 76, No. 18, May 1, 2000, pp. 2523-2525.

* cited by examiner

HYBRID SPHERE-WAVEGUIDE RESONATORS

FIELD OF THE INVENTION

The present invention is directed generally to optical devices, and more particularly to passive and active optical devices such as optical sensors, filters and micro-lasers, based on microresonators.

BACKGROUND

Dielectric microresonators have attracted increasing attention in opto-electronic and sensing applications, including biosensing. One common configuration of microresonator involves a glass microsphere, typically 20 μm to a few millimeters in diameter, which is put into close proximity to an optical waveguide such as an optical fiber that has been heated and tapered, or etched to a total thickness of 1-5 μm.

The tapering modifications to the fiber result in there being a substantial optical field intensity outside the fiber, and thus light can couple into the microsphere and excite its eigenmodes, often referred to as whispering gallery modes (WGMs). When microresonators are made with low loss materials and have a high surface quality, the propagation loss of light propagating in WGMs may be very low, and extremely high quality factors, also known as Q-factors, can be achieved: values as high as $10^9$ are achievable. Due to the high Q-factor, the light can circulate inside the microresonator for a long time, thus leading to a large field enhancement in the cavity mode, and a long effective light path. This makes such devices useful for linear, non-linear and optical sensing applications.

There are practical difficulties in realizing the fiber-microsphere combination described above. First, the fiber must be tapered to a few microns in diameter. This commonly results in a relatively long (a few cm) and fragile tapered region. Second, the relative position of the microsphere and the fiber taper must be held constant to within a few nanometers if the optical coupling and the Q-factor are to remain constant. This is difficult with a free sphere and thinned fiber.

Other forms of micro-optical resonators have used a disk, or ring, rather than a sphere as the optical resonant cavity, where the disk and waveguide are fabricated on the same planar substrate. This monolithic approach is typically realized in semiconductor waveguides, and provides excellent stability of coupling between the waveguides and the resonator. The etching process used to fabricate the disk resonator, however, invariably introduces surface roughness, that results in a scattering loss that severely degrades the Q of the cavity. Cavities formed using this approach typically have a Q-factor value of around a few thousand.

Another approach is to suspend a glass microsphere above the surface of a channel waveguide fabricated on a planar substrate, so that the optical coupling between the sphere and the waveguide takes place in the vertical direction. This approach preserves the high Q-factor of the glass microsphere, but does not solve the problem of how to precisely control the coupling between the microsphere and the waveguide.

SUMMARY OF THE INVENTION

There remains a need to increase the stability of the position of the microcavity, be it a planar or spherical cavity, relative to the waveguide, while still maintaining high cavity Q and ease of launching and extracting the optical beams.

One particular aspect of the invention described here is directed to provide structures on a substrate that are useful for maintaining the position of the microresonator relative to the waveguide or waveguides used to couple the light into and out of the microresonator.

One particular embodiment of the invention is directed to a microresonator device that comprises a first substrate having at least one self-aligning feature on a surface and a first waveguide disposed relative to the first substrate. A microresonator is positioned on the substrate by the self-aligning feature so as to optically couple to the first waveguide.

Another embodiment of the invention is directed to a method of making a microresonator optical device. The method includes providing at least one self-aligning feature on a first substrate and providing a first waveguide. A microresonator is positioned, using the at least one self-aligning feature, so that the microresonator is in an optically coupling relationship with the first waveguide.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
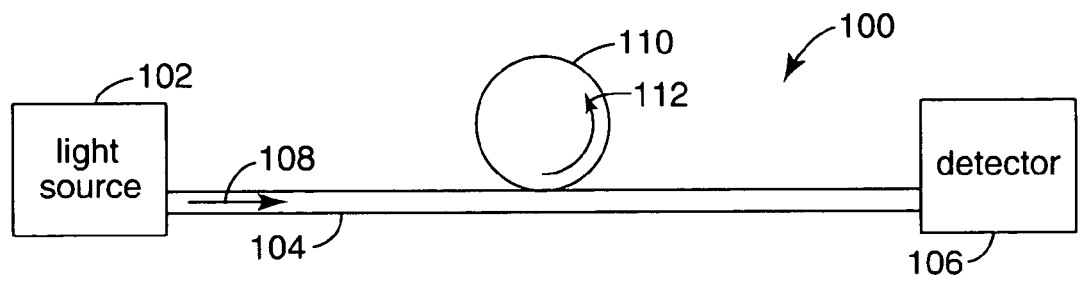
FIGS. 1A and 1B schematically illustrate embodiments of a microsphere resonator optical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is applicable to passive and active optical devices, such as sensors, filters, amplifiers, and/or micro-lasers, that use microresonators, such as microspheres and micro-planar ring cavities. The invention is believed to be particularly useful for fabricating such devices, in that the relative positions of the microresonator and the waveguide are controlled, the microresonator Q-factor can be high, and there is ease in launching and receiving the optical beam.

A microsphere-waveguide system 100 that uses a microresonator is schematically illustrated in FIG. 1A. A light source 102 directs light along a waveguide 104 to a detector unit 106. The microresonator 110 is optically coupled to the waveguide 104. Light 108 from the light source 102 is launched into the waveguide 104 and propagates towards the detector unit 106. The microresonator 110 evanescently couples some of the light 108 out of the waveguide 104, the out-coupled light 112 propagating within the microresonator 110 at one of the resonant frequencies of the microresonator 110.

The light source 102 may be any suitable type of light source. For increased efficiency and sensitivity, it is advantageous that the light source produces light that is efficiently coupled into the waveguide 104, for example the light source may be a laser such as a laser diode. The light source 104 generates light 108 at a desired wavelength. For example, where the microresonator is used in a sensor, the light source 102 generates light at a wavelength that interacts with the species being sensed. The species being sensed is typically located in proximity to the surface of the microresonator 110 so that the light propagating in the WGM interacts with the species being sensed. In another example, where the microresonator 110 is used as a microlaser, the light source 102 typically operates at a wavelength suitable for optically pumping an excitable medium doped in the microresonator 110.

The light source 102 may direct light into a number of different waveguides, of which the waveguide 104 is one. The waveguide 104 may be any suitable type of waveguide and may be, for example, a planar waveguide or a channel waveguide formed in or on a substrate, such as a waveguide formed in a silica substrate. The waveguide 104 may also be an optical fiber.

The detector unit 106 includes a light detector, for example a photodiode or phototransistor, to detect light. The detector unit 106 may also include a wavelength sensitive device that selects the wavelength of light reaching the light detector. The wavelength selective device may be, for example, a filter, or a spectrometer. The wavelength selective device, for example a spectrometer, may be tunable so as to permit the user to actively change the wavelength of light incident on the light detector.

The microresonator 110 may be positioned in physical contact with, or very close to, the waveguide 104 so that a portion of the light 106 propagating along the waveguide 104 is evanescently coupled into the microresonator 110. The waveguide 104 typically has little or no cladding at the point where the microresonator 110 couples to the waveguide 104, so that the micro-resonator 110 couples directly to the core of the waveguide 104.

Figure 1B:
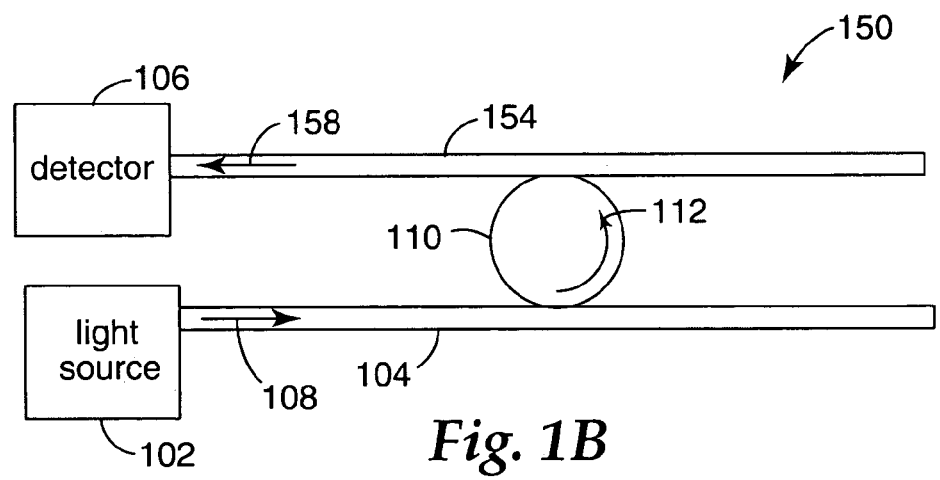

Another type of microresonator device 150 is schematically illustrated in FIG. 1B. In this device 150, light 158 from the microresonator 110 is coupled into a second waveguide 154, and propagates to the detector 106. In this configuration, the detector 106 only detects light that has been coupled from the microresonator 110.

Figure 2:
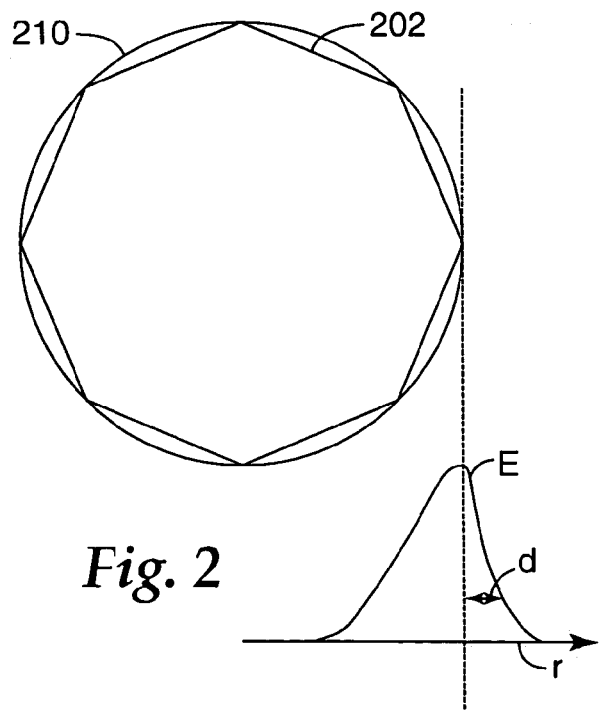
FIG. 2 shows a schematic representation of internal reflections within a microsphere and the electric field distribution of the whispering gallery mode inside and outside the microresonator.

Light propagates within the microresonator in so-called "whispering gallery modes", an example of which is schematically illustrated in FIG. 2. In a whispering gallery mode (WGM) 202, the light propagates around the micro-resonator 210 from an origin via a number of total internal reflections, until it returns to the origin. In the illustrated embodiment, the WGM 202 includes eight total internal reflections in a single round trip. It will be appreciated that the light may propagate within the micro-resonator 210 in other WGMs that correspond to different numbers of total internal reflections.

Furthermore, the WGM of the microresonator 210 is a mode for light whose wavelength is equal to an integral fraction of the round trip length of the whispering gallery mode. Stated another way, the WGM only demonstrates a high Q-factor where the light is of such a wavelength that it constructively interferes after one round trip. This resonant condition can be stated mathematically as:

$$\lambda_m = L/m \qquad (1)$$

where $\lambda_m$ is the wavelength of the mth mode, L is the optical length of one round trip of the WGM, and m is an integer, referred to as the mode number. Light from the waveguide 104 that satisfies the resonant condition (1) is efficiently coupled to the microresonator.

The electric field intensity of the WGM peaks at the interior surface of the micro-resonator 210. The electric field intensity of the WGM decays exponentially outside the micro-resonator 210, with an exponential decay factor, d, given by $d \approx \lambda/n$ where $\lambda$ is the wavelength of the light in vacuum and n is the refractive index of the medium outside the micro-resonator 210. The field intensity, E, is schematically illustrated in FIG. 2 for the WGM 202 along the cross-section line AA'.

The microresonator is small, typically having a diameter in the range from 20 μm to a few millimeters. Furthermore, the waveguide is often tapered to increase the intensity of the optical field intensity outside the waveguide, thus increasing the amount of light that couples into the microresonator. In the case of an optical fiber waveguide, the fiber is heated and tapered or etched to a total thickness of about 1-5 μm. Likewise, with a planar or channel waveguide, the waveguide thickness may be reduced at the region where the light is coupled to the microresonator. In addition to the waveguide being reduced in size, the thickness of the cladding around the waveguide may also be reduced.

This leads to some practical difficulties in assembling the microresonator sensor unit. For example, in the case of a fiber waveguide, the fiber is tapered to a few microns in diameter, which leads to a relatively long tapered region, typically a few cm in length, which is also fragile. Also, the relative positions of the microresonator and the waveguide should be held constant, typically to within a few nanometers, to maintain a constant degree of optical coupling between the waveguide and the microresonator. This is difficult with a free microsphere and a thinned fiber waveguide.

In the present invention, an approach to maintaining a constant level of optical coupling between the microresonator and the waveguide, while allowing the use of a high Q-factor microresonator, includes using a substrate that has at least one self-aligning feature on a surface. The waveguide is disposed relative to the first substrate, and the microresonator is positioned on the substrate by the self-aligning feature so as to optically couple to the first waveguide.

Figure 3A:
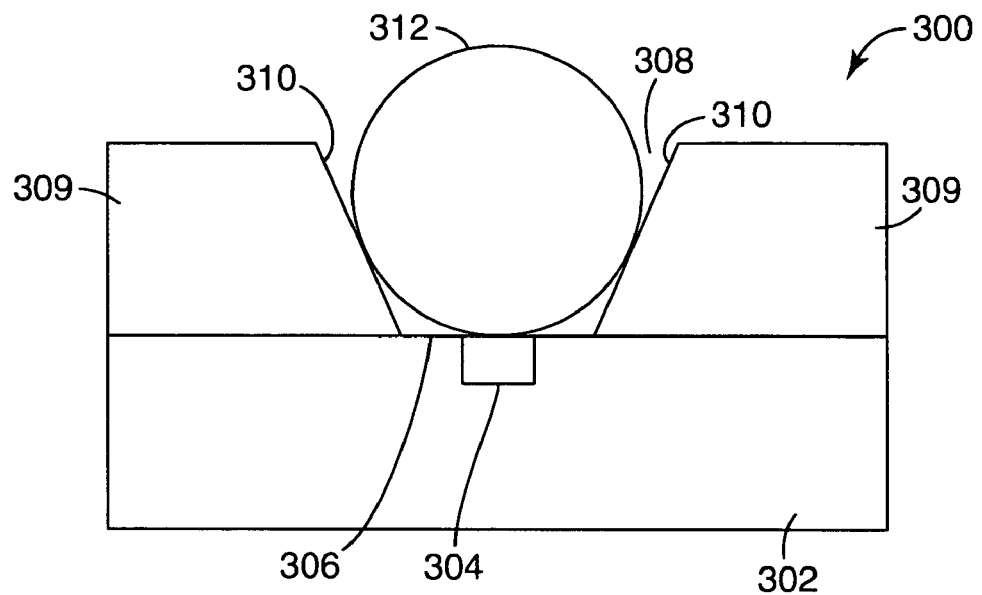
FIGS. 3A-3F schematically illustrate embodiments of a microsphere resonator device according to principles of the present invention.
Figure 3B:
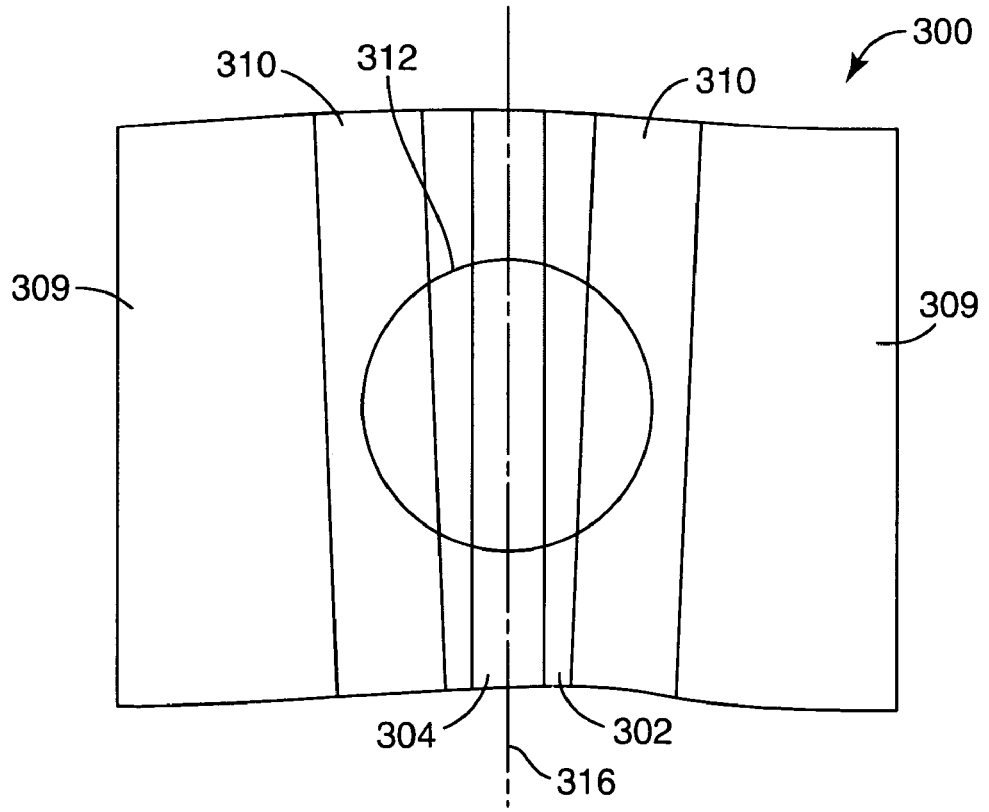

One particular embodiment of the present invention is schematically illustrated as device 300 in FIGS. 3A and 3B. In this example, a substrate 302 with a planar waveguide 304 is formed on a surface 306. A self-aligning feature 308, shown here in the form of an aligning groove, or slot, having sloped sidewalls 310, is provided over the surface 306. The sidewalls 310 guide the position of the microresonator 312 transverse to the waveguide 304. In this particular example, the lateral position of the microresonator 312 relative to the waveguide 304 may be determined by contact points on the sidewalls 310. The sidewalls 310 that form the groove maybe walls of shims or other structures 309 formed on the surface 306. The structures may be cast, or otherwise formed, on the surface 306 or may be formed separately from the surface 306 and then attached to the surface.

The sidewalls 310 may be positioned to be parallel to the waveguide 304. Since achieving parallelism between the waveguide 304 and the sidewalls 310 may be difficult, the sidewalls 310 may be positioned to be non-parallel to the waveguide 304. In one particular embodiment, illustrated in FIG. 3B, the sidewalls 310 are not parallel to the waveguide 304 or to each other. This configuration permits the microresonator 312 to be aligned to the waveguide 304 and the sidewalls by rolling the microresonator 312 along the waveguide 304 within the sidewalls 310 until contact is made between the microresonator 312 and the sidewalls 310, and there is still optical coupling between the microresonator 312 and the waveguide 304. In another embodiment, not shown, the sidewalls may be parallel to teach other but not parallel to the waveguide.

Figure 3C:
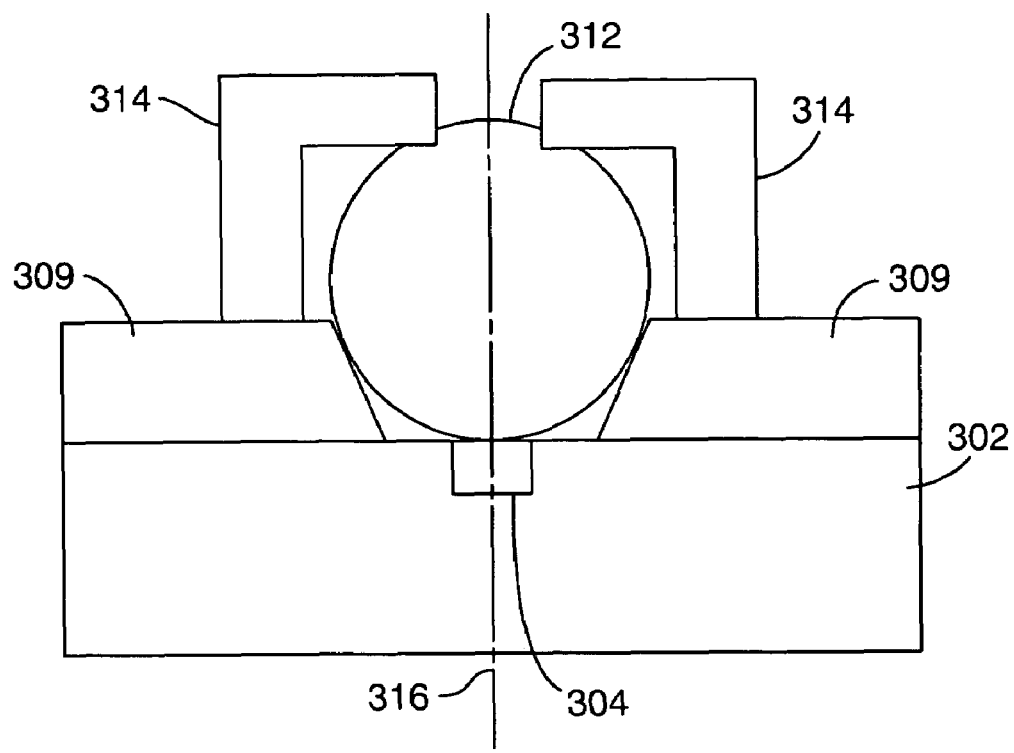

The microresonator 312 may be held in position relative to the waveguide 304 in several different ways. For example, the groove 310 may be filled, or at least partially filled, using an adhesive (not shown) to hold the microresonator 312 in place. Another approach is schematically presented in FIG. 3C, which shows the microresonator 312 held in place with one or more holding devices, such as retaining members 314. The retaining members 314, for example, can be formed from a polymer-based material applied to the structures 309 or to a surface of the substrate 302. In an exemplary embodiment, the holding device that positionally retains the microresonator 312 relative to the waveguide 304 does not contact the microresonator 312 at a position on the plane of light propagation within the microresonator 312. In the illustrated example, the plane of light propagation forms a plane perpendicular to the plane of FIGS. 3B and 3C, at the line 316. The plane of light propagation within the microresonator 312 is determined by the direction in which the light enters the microresonator 312 from the waveguide 304. The WGMs excited by the waveguide 304 lie in the plane of light propagation. If the holding device touches the outer surface of the microresonator 312 at the plane of light propagation, then the Q-factor of the microresonator cavity may be reduced, thus reducing the sensitivity of the microresonator sensor.

Figure 3D:
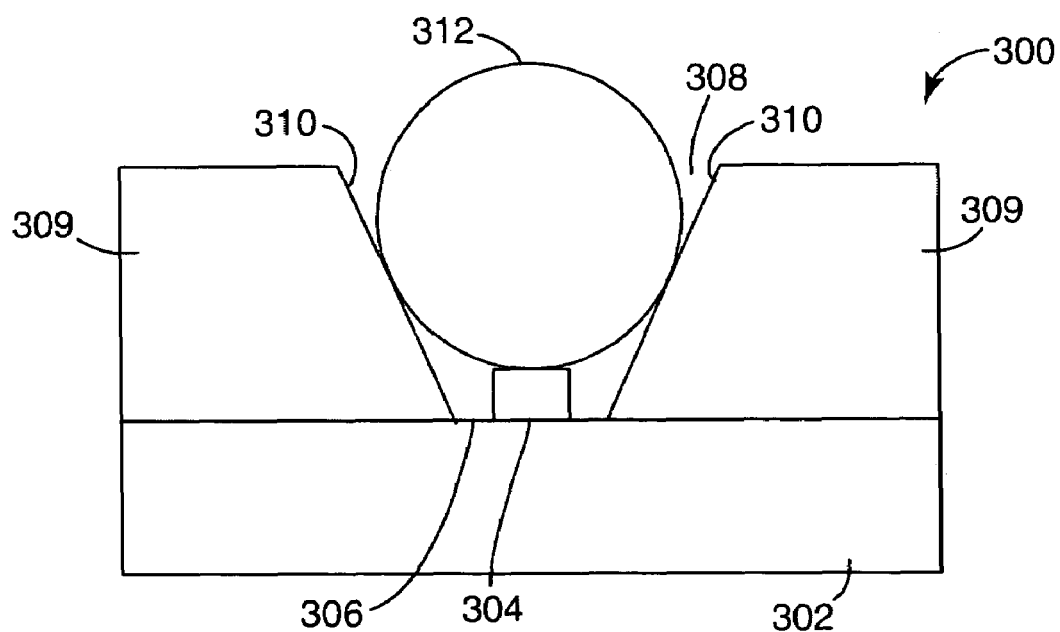
Figure 3E:
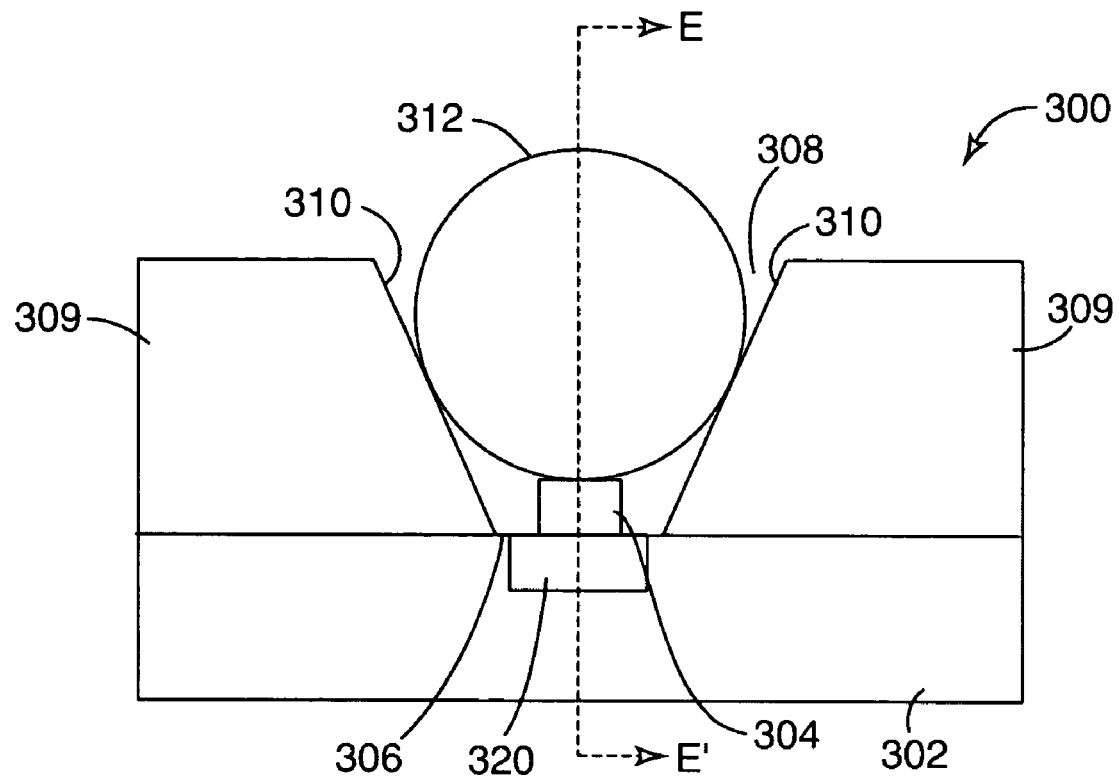
Figure 3F:
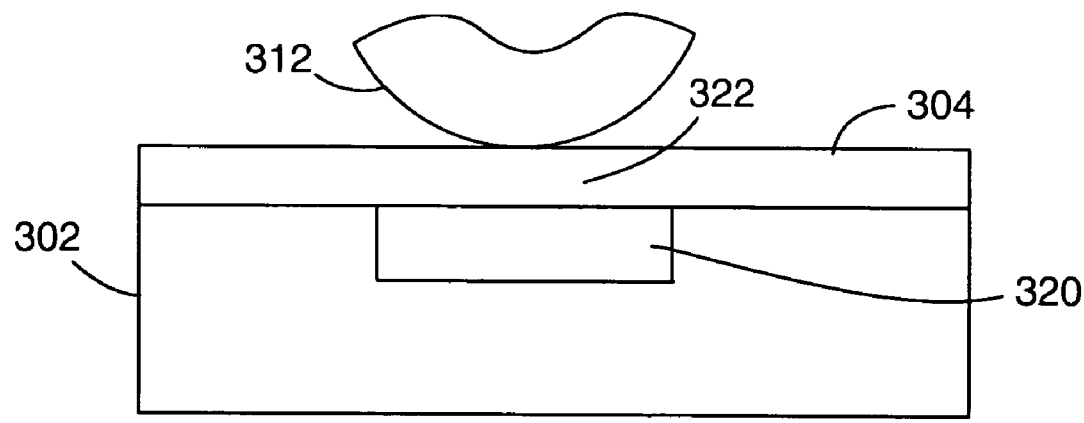

Other embodiments, in which the waveguide is a channel waveguide, are now described with reference to FIGS. 3D-3F. In FIG. 3D, the waveguide, 304 may be a channel waveguide disposed above the surface 306 of the substrate 302. The sidewalls 310 laterally align the microresonator 312 relative to the waveguide 304. The microresonator 312 may rest on the waveguide, as illustrated, or may be held out of contact with the waveguide 304.

The refractive index of the cladding, in this case the substrate 302, below the point on the waveguide 304 that couples to the microresonator 312 may be reduced. This reduces the extent of the electric field extending into the substrate, and results in an increase in the intensity of the electric field on the upper side of the waveguide 304 that couples to the microresonator 312. The refractive index may be reduced, for example, by doping the substrate 302.

Another approach to reducing the refractive index of the waveguide cladding at the point of coupling between the waveguide 304 and the microresonator 312 is to remove some of the substrate material to leave a void 320 below the waveguide 304. This is shown in FIGS. 3E and FIG. 3F, which shows a partial cross-section of device along the section EE' shown in FIG. 3E. This results in a portion 322 of the waveguide 304 forming a bridge over the void 320.

Figure 4A:
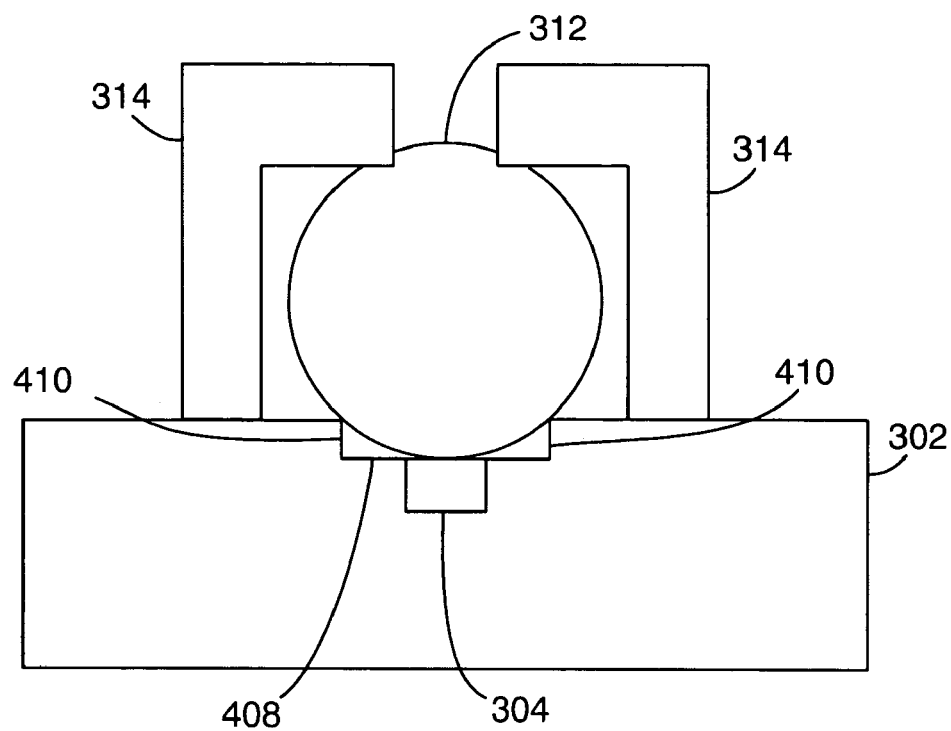
FIGS. 4A and 4B schematically illustrate another embodiment of a microsphere resonator device according to principles of the present invention.
Figure 4B:
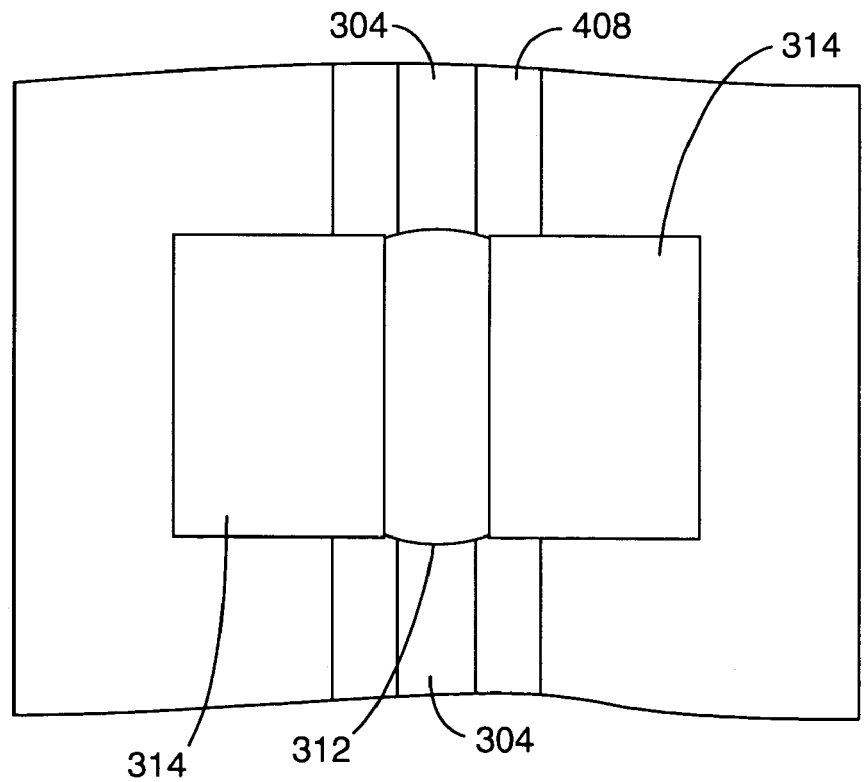

The self-aligning feature need not be a groove with sloped sidewalls, but may take on other geometries. For example, as schematically illustrated in FIGS. 4A and 4B, the self-aligning feature 408 may be a groove having vertical sidewalls 410. In this particular example, the lateral position of the microresonator 312 is determined by the top edges of the sidewalls 410.

Given the present description, it will be appreciated that self-aligning features may also have other geometries. For example, a self-aligning feature may include a groove having more surfaces than two sides, or two sides and a bottom surface. One such example is a groove having four or more surfaces.

As mentioned above, the microresonator optical device of one or more of the embodiments present invention can be designed for passive and active applications. For example, the optical device may be utilized as a filter or sensor. In addition to the other sensing embodiments described herein, in biosensing applications, microresonator can be coated with one or more antibodies, proteins, or other biological samples. A detector may be used to sense variations in optical output or fluorescence emanating from the biological materials. Active applications, such as amplifier and microlaser applications, can be accomplished by, for example, doping the microresonator 312 with one or more materials, such as erbium, to create a gain medium. In a laser application, light having a first wavelength (e.g., 980 nm) from the light source can be evanescently coupled to the microresonator to optically pump the microlaser, with light of a second wavelength, for example, about 1550 nm, being output from the microresonator. As will be apparent, given the present description, the optical device 300 can be modified depending on the particular application needed.

According to another exemplary embodiment, a microresonator optical device having two waveguides coupled to the microresonator is described with reference to FIG. 5. In this particular embodiment, the microresonator 512 is sandwiched between two substrates 502a and 502b separated by an intermediate member 510. Each of the substrates 502a and 502b is provided with self-aligning features 508a and 508b for aligning the microresonator 512 to the waveguides 504a and 504b on the respective substrates 502a and 502b. This type of sensor unit permits the light to be directed into the microresonator 512 via a first waveguide, for example, 504a, and also permits the light to be detected via a second waveguide, for example 504b.

Figure 5:
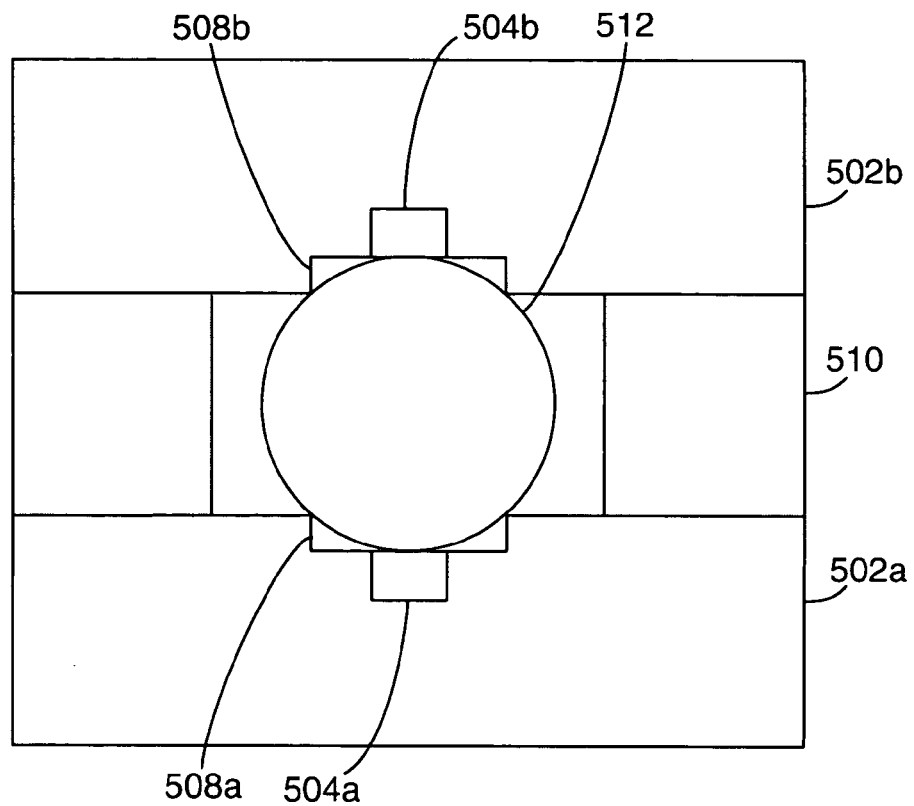
FIG. 5 schematically illustrates another embodiment of a microsphere resonator device according to principles of the present invention.

It will be appreciated that the scope of the present invention is intended to cover variations on the embodiment illustrated in FIG. 5. For example, the intermediate member 510 need not be present, and the substrates 502a and 502b may or may not contact each other. Furthermore, there may be an additional member for holding the microresonator 512. Also, the self-aligning features 508a and 508b need not have vertical sidewalls, but may adopt different geometries. In addition, the self-aligning features 508a and 508b need not have the same geometry, and the microresonator 512 may or may not be in direct physical contact with the waveguides 504a and 504b.

Figure 6A:
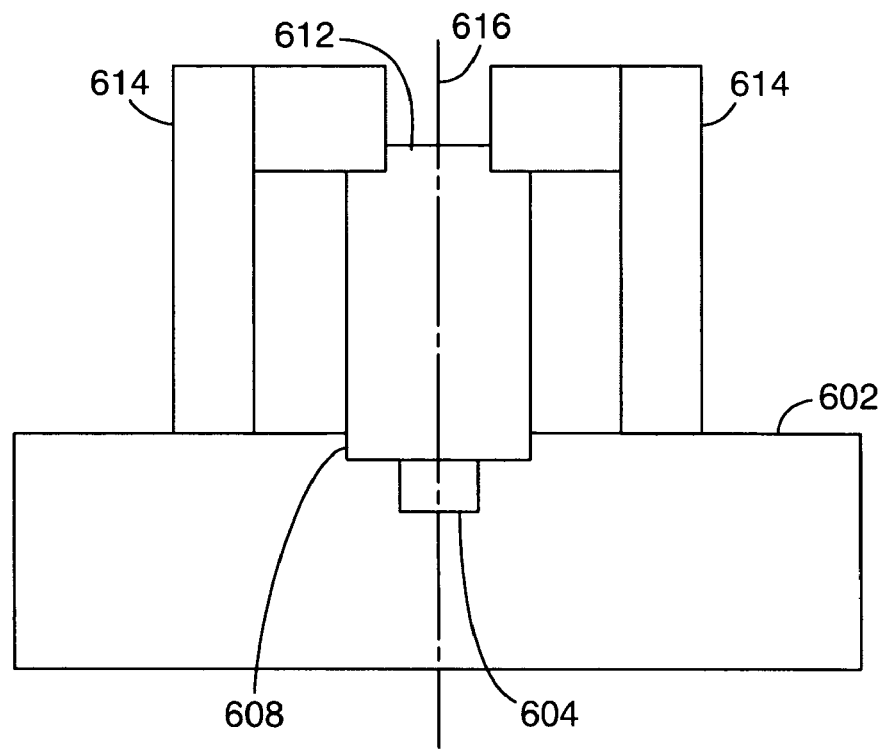
FIGS. 6A and 6B schematically illustrate another embodiment of a microsphere resonator device according to principles of the present invention.
Figure 6B:
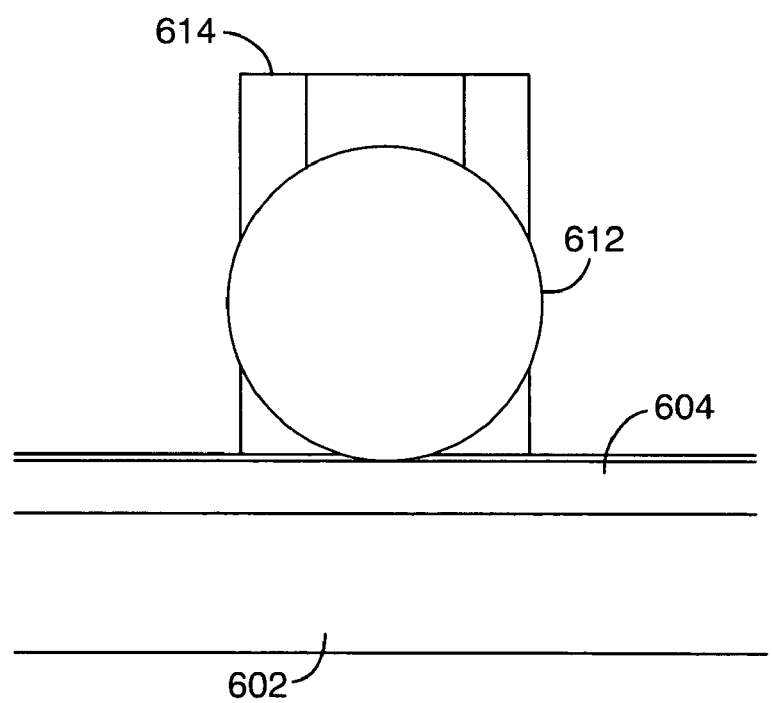

In another embodiment, schematically illustrated in FIGS. 6A and 6B, the microresonator may be planar, for example where it may be taken as a section from an optical fiber. If taken as a fiber section, the fiber section is viewed side-on in FIG. 6A. The plane of the planar microresonator 612 is parallel to the light plane 616. In this particular embodiment, the substrate 602 has a self-aligning feature 608 in the form of a groove that constrains the planar microresonator 612 to a particular lateral position relative to the waveguide 604. The planar microresonator may be held in place using any suitable method for example using an adhesive (not shown), or one or more holding members 614. FIG. 6B schematically illustrates a cross-section of the sensor unit in the light propagation plane 612.

Figure 7A:
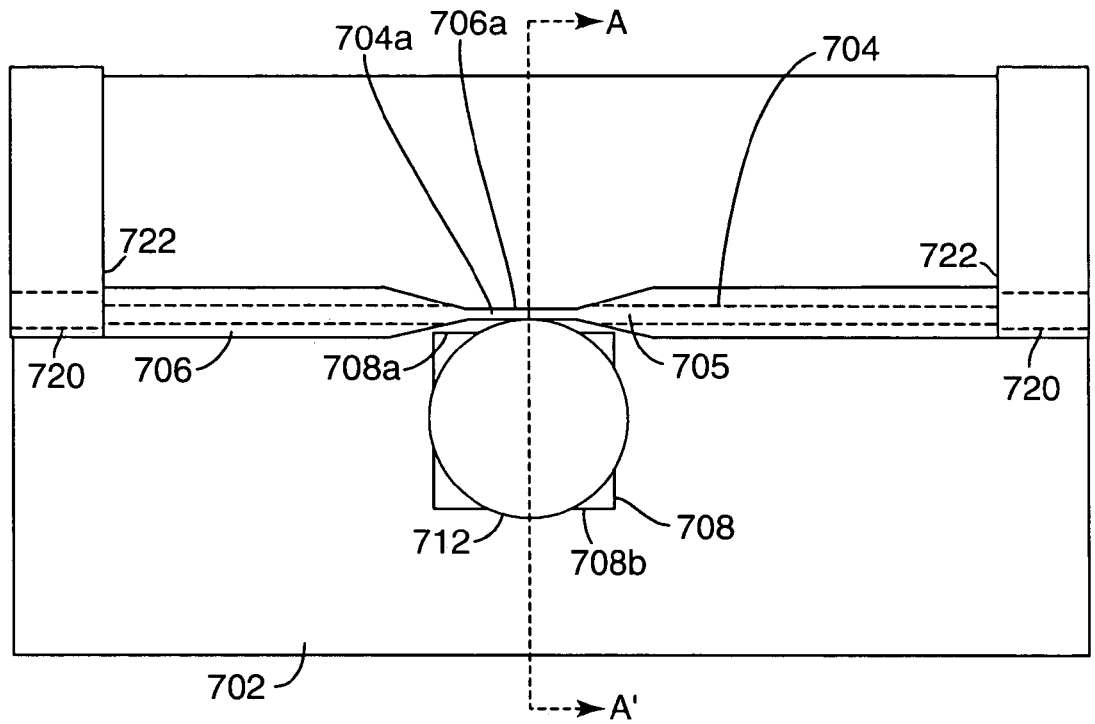
FIGS. 7A-7D schematically illustrate other embodiments of a microsphere resonator device according to principles of the present invention.
Figure 7B:
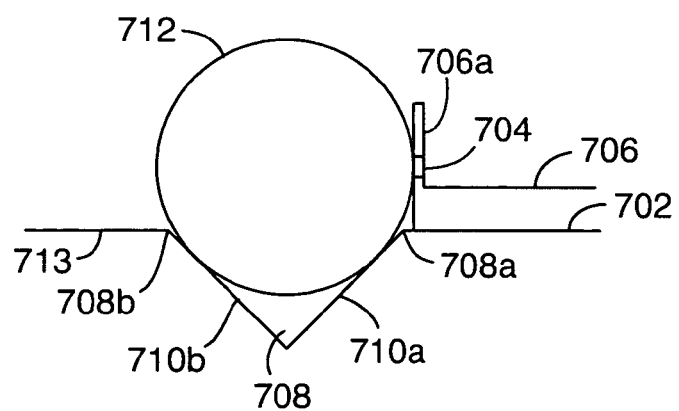

Another approach to assembling a microresonator optical device is now described with reference to FIGS. 7A-7D. FIG. 7A schematically shows a plan view of the device, while FIG. 7B schematically shows a partial cross-section at AA'. In the illustrated embodiment, a waveguide 704 is formed or mounted on the substrate 702 with an accessible surface 705 facing horizontally across the substrate 702.

A self-aligning feature 708, illustrated as a well or cavity having sloped sidewalls 710, is provided on a surface of the substrate 702. A microsphere 712 may be located by the self-aligning feature 708 in a position so that optical coupling takes place between the microsphere 712 and the waveguide 704. It will be appreciated that the self-aligning feature 708 need not have sloped sidewalls, but may have, for example, vertical sidewalls.

The waveguide 704 is formed within a cladding 706. That portion of the waveguide 704 having the accessible surface 705 may be tapered to be smaller than other parts of the waveguide, for example at tapered waveguide portion 704a. There is no restriction on which sides of the waveguide 704 may be tapered. For example, the waveguide 704 may be tapered both at the front side, facing the microresonator 712, and at the back side. Also, the height of the waveguide 704 may be tapered in the tapered region. In this manner, the intensity of the electric field outside the waveguide 704 may be increased, thus ensuring better optical coupling from the waveguide 704 to the microresonator 712. In addition, the cladding 706 may be tapered, for example at tapered region 706a, so as to increase the magnitude of the optical field that couples between the waveguide 704 and the microresonator 712. Also, the waveguide 704 may be coupled to optical fibers 720 at fiber couplers 722, or to other waveguides for coupling light to and from the light source and the detector.

Figure 7C:
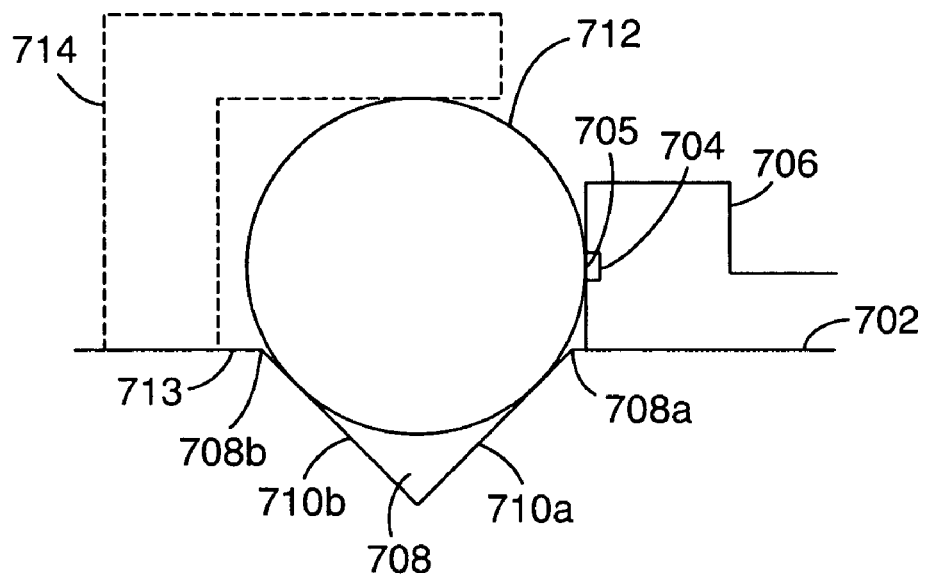

The microresonator 712 may be held in the self-aligning feature using several different approaches. One approach is to apply an adhesive (not shown) to fix the microresonator 712 to the substrate 702. The adhesive may, for example, be positioned within the cavity 708, or may attach the microresonator 712 to the upper surface of the substrate 702. Optionally, a holding member 714, shown in dashed lines in FIG. 7C, may be used to hold the microresonator 712 in place. Also, FIG. 7C shows an embodiment where the cladding 706 is tapered only from one side at the coupling region.

Certain considerations may need to be taken into account when the microresonator 712 contacts both edges 708a and 708b of the self-aligning feature 708. The position of the waveguide 704 relative to the feature 708 can depend on several factors, such as the radius of the microresonator 712, the height of the waveguide 704 above the surface 713, the size of the aligning feature 708 and the slope of the sidewalls 710a and 710b. For example, the waveguide 704 may be recessed away from the edge 708a, set at the edge 708a or may be cantilevered over the edge 708a in order to bring the waveguide 704 into more optimal optical coupling with the microresonator 712. This particular approach may be useful when it is desired to hold the microresonator at a controlled distance from the edge of the waveguide.

One approach that may be useful for increasing the electric field at the front of the waveguide 704, and thus increasing the amount of optical coupling between the waveguide 704 and microresonator 712, is to reduce the effective refractive index of the cladding 706 at the tapered waveguide region 704a. This may be done by doping the cladding 706 or by reducing the thickness of the cladding 706a along the waveguide 704 in the region where the waveguide 704 optically couples to the microresonator 712. This latter approach is schematically illustrated in FIG. 7B.

Figure 7D:
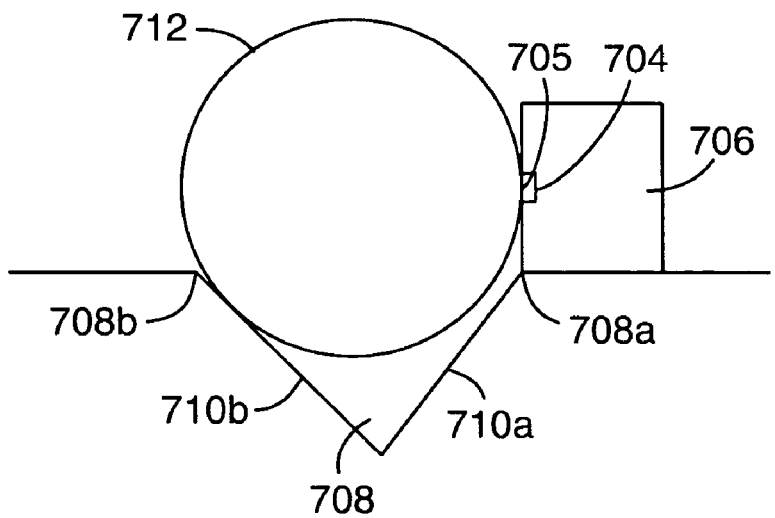

Another approach is schematically illustrated in FIG. 7D, where the microresonator 712 is held between the waveguide 704 and the rear sidewall 710b, and does not touch the front sidewall 710a. This arrangement may be referred to as an over-constrained arrangement. One of the advantages of such an arrangement is to increase the probability of good physical contact between the waveguide 704 and the microresonator 712.

Figure 8:
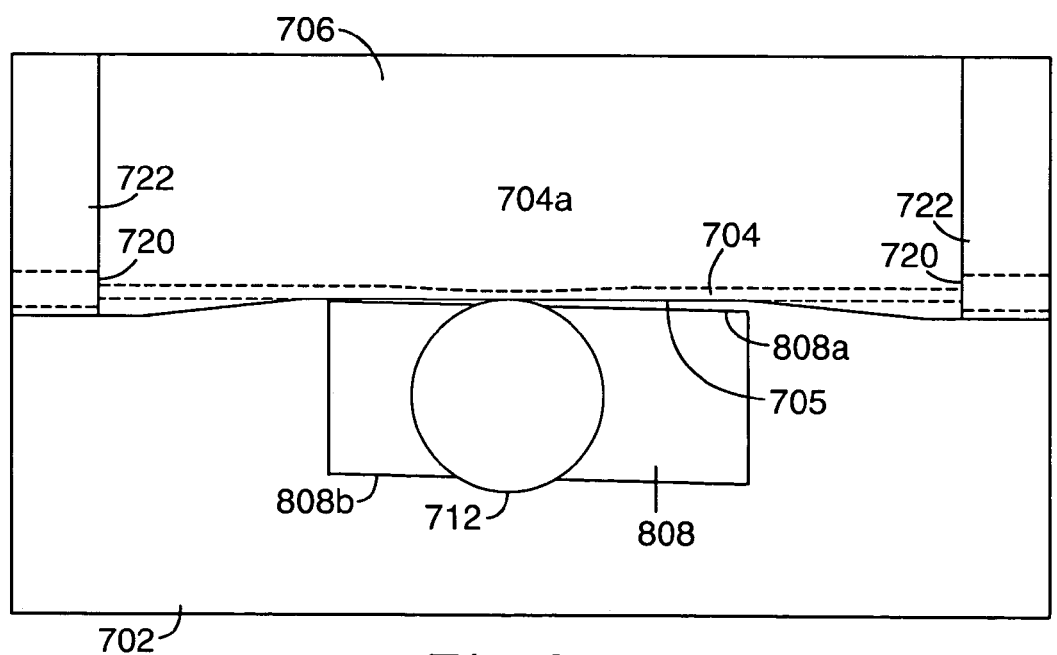
FIG. 8 schematically illustrates another embodiment of a microsphere resonator device according to principles of the present invention.

It will be appreciated that the shape of the self-aligning feature 708 need not be square, as shown in FIG. 7A, but may take on other shapes. For example, the self-aligning feature 808 may be elongated in a direction substantially parallel with the waveguide 704, as is schematically illustrated in FIG. 8. Here, the self-aligning feature is longer in the direction parallel to the waveguide 704, forming a groove or slot. In addition, it will be appreciated that the edges 808a and 808b of the feature 808 need not both be parallel to the waveguide 704. Where the edges 808a and 808b are parallel to each other, but not parallel to the waveguide 704, as illustrated, the distance between the microresonator 712 and the waveguide 704 may simply be adjusted by moving the microresonator 712 along the feature 808.

In another embodiment of an over-constrained arrangement, only one edge, such as the back edge 808b, may be non-parallel to the waveguide 704. This provides flexibility in the positioning of the microresonator 712 relative to the waveguide 704.

Figure 9A:
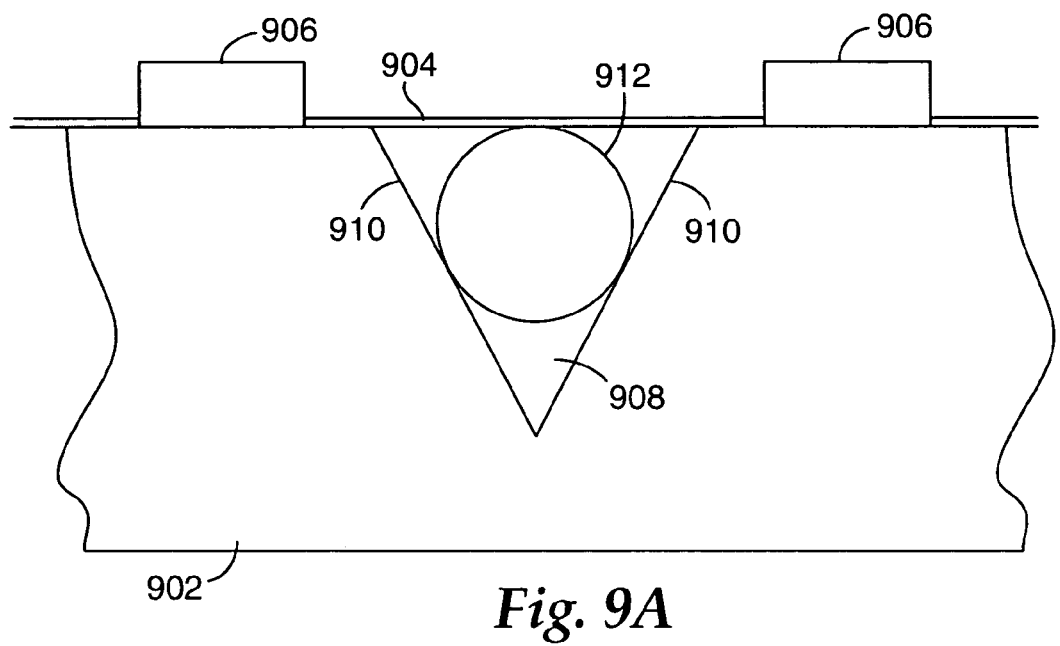
FIGS. 9A and 9B schematically illustrate another embodiment of a microsphere resonator device according to principles of the present invention.
Figure 9B:
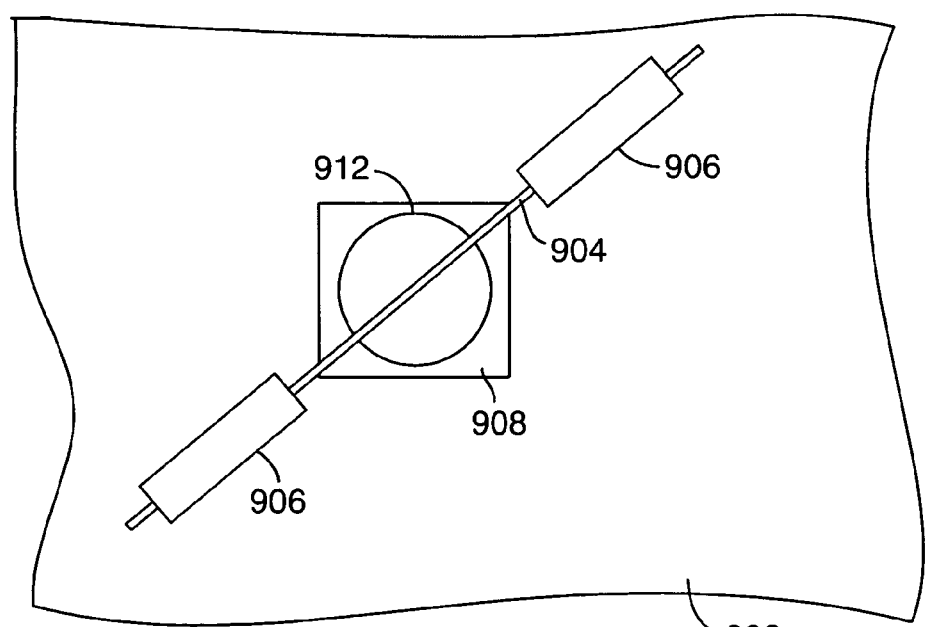

It will be appreciated that self-aligning features need not only be used along with planar waveguides, but also with fiber waveguides. One example of such an arrangement is schematically illustrated in FIGS. 9A and 9B. A self-aligning feature 908 is formed in a substrate 902 to hold a microresonator 912. A fiber waveguide 904 is placed over the microresonator 912 and held in place via fiber mounts 906. In the illustrated embodiment, the self-aligning feature 908 is a cavity or well, having sloped sidewalls 910. The fiber waveguide 904 may be arranged so that it is not parallel to the edges of the feature 908. Consequently, the plane of light propagation within the microresonator 912 does not intersect any of the points where the surface of the microresonator contacts the sidewalls 910: this configuration may help to maintain a high Q-factor for the microresonator.

The microresonator 912 may be held in the cavity 908 using an adhesive, a holding member, a combination of the two, or using some other method. It will be appreciated that the self-aligning feature need not have sloped sidewalls, but may have curved or vertical sidewalls. Furthermore, the shape of the feature 908 need not be square, as shown in FIG. 9B, but may have some other shape.

The top of the microresonator 912 may be flush with the upper surface of the substrate 902, or may protrude higher than the surface of the substrate 902. Furthermore, the fiber waveguide 904 may be positioned over the microresonator 912 under some tension so as to maintain close physical contact between the fiber waveguide 904 and the microresonator 912.

Figure 10A:
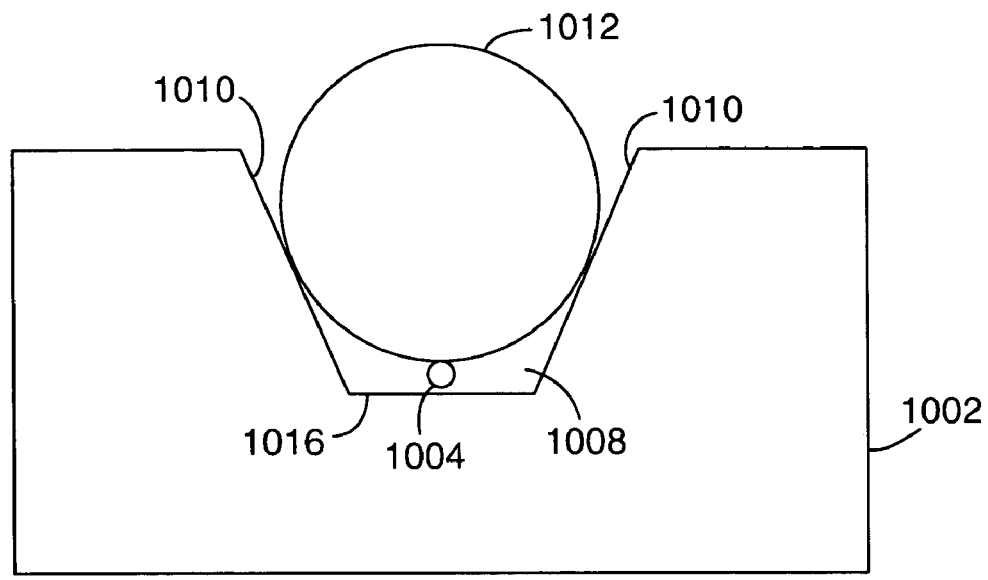
FIGS. 10A and 10B schematically illustrate another embodiment of a microsphere resonator device according to principles of the present invention.
Figure 10B:
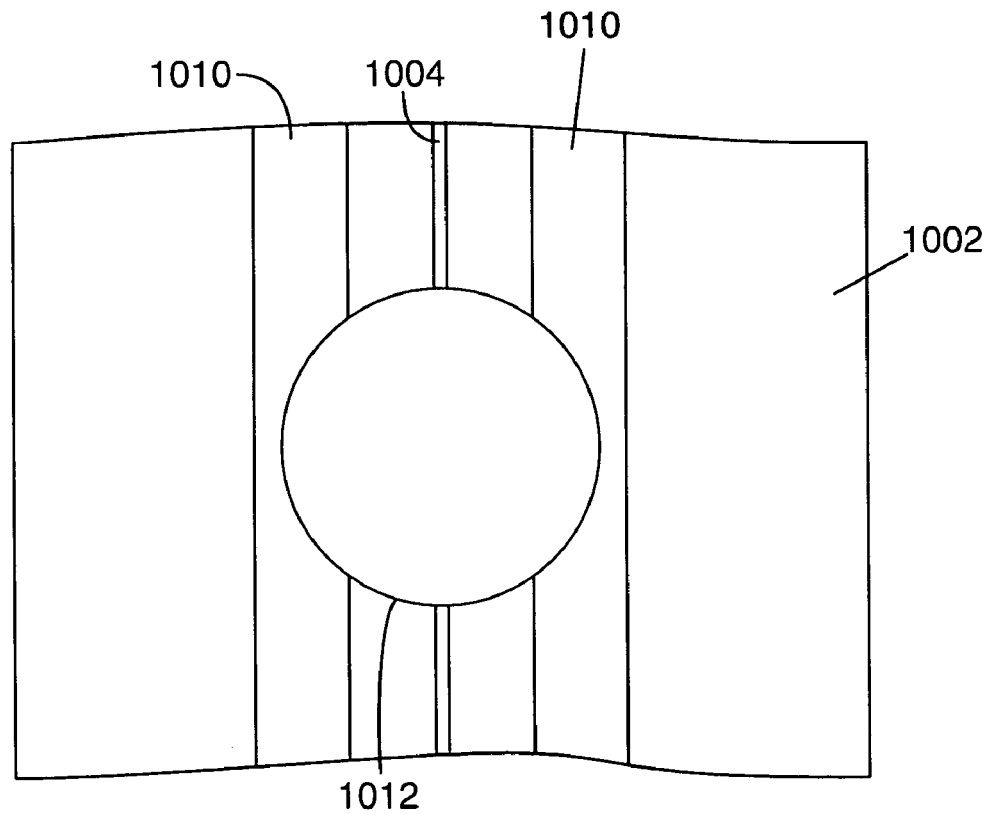

Another approach to vertical optical coupling between the fiber waveguide and the microresonator is schematically illustrated in FIGS. 10A and 10B. In this embodiment, the fiber waveguide 1004 is positioned within the alignment feature 1008 formed on the substrate 1002. The alignment feature 1008 is illustrated to be in the form of a groove with sloping sidewalls 1010, although the sidewalls may also be vertical. The microresonator 1012 is constrained laterally relative to the fiber waveguide 1004. Furthermore, the microresonator 1012 may be held into the groove 1008, for example, using adhesive or a holding member, to maintain optical coupling between the waveguide 1004 and the microresonator 1012. The fiber waveguide 1004 may be held out of contact with the lower surface 1016 of the groove, for example using mounts (not shown) on the lower surface 1016. If the mounts are positioned away from that portion of the waveguide 1004 where the magnitude of the optical field outside the waveguide core is high, in other words the coupling region of the waveguide 1004, then the optical losses associated with the mounts may be reduced. This configuration reduces optical losses that might otherwise result from the tapered section of fiber touching the lower surface 1016.

In another embodiment (not shown), two fiber waveguides may be coupled to the microresonator, for example in a manner similar to that illustrated in FIG. 5, by providing separate substrates, with associated fiber waveguides, on either side of the microresonator.

Figure 11A:
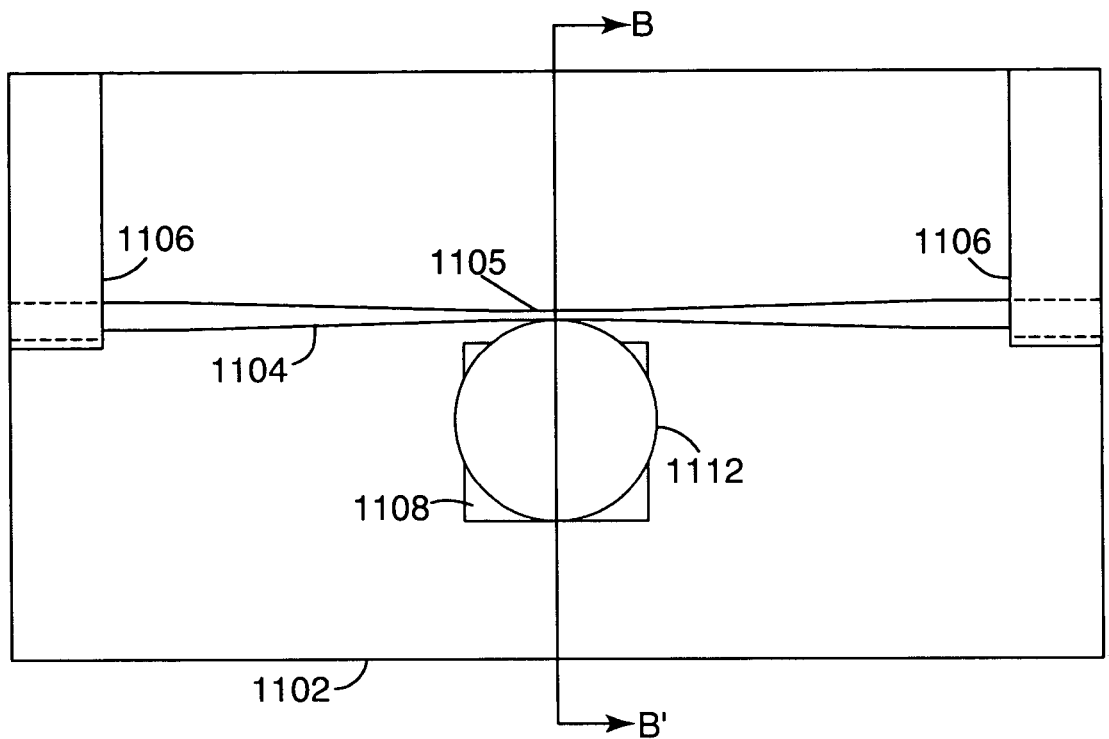
FIGS. 11A and 11B schematically illustrate another embodiment of a microsphere resonator device according to principles of the present invention.
Figure 11B:
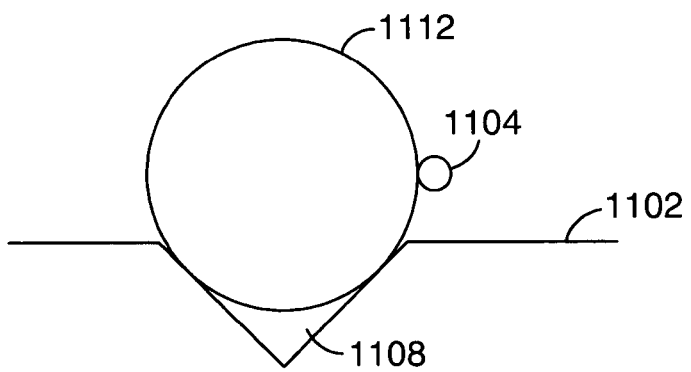

Self-aligning features may also be used on a substrate to provide horizontal optical coupling between a fiber waveguide and the microresonator, for example as is schematically illustrated in FIGS. 11A and 11B. FIG. 11A shows a plan view while FIG. 11B shows a partial cross-sectional view at the section BB'. In this particular embodiment, a substrate 1102 is provided with a fiber waveguide 1104 held between two fiber holders 1106. An alignment feature 1108, illustrated as a cavity, positions a microresonator 1112 very close to, or in contact with, a fiber waveguide 1104. The portion of the fiber waveguide 1104 in contact with the microresonator 1112 is typically a tapered section 1105. The microresonator 1112 may be held in place relative to the alignment feature 1108 using any suitable method, for example an adhesive or a holding member.

Figure 12:
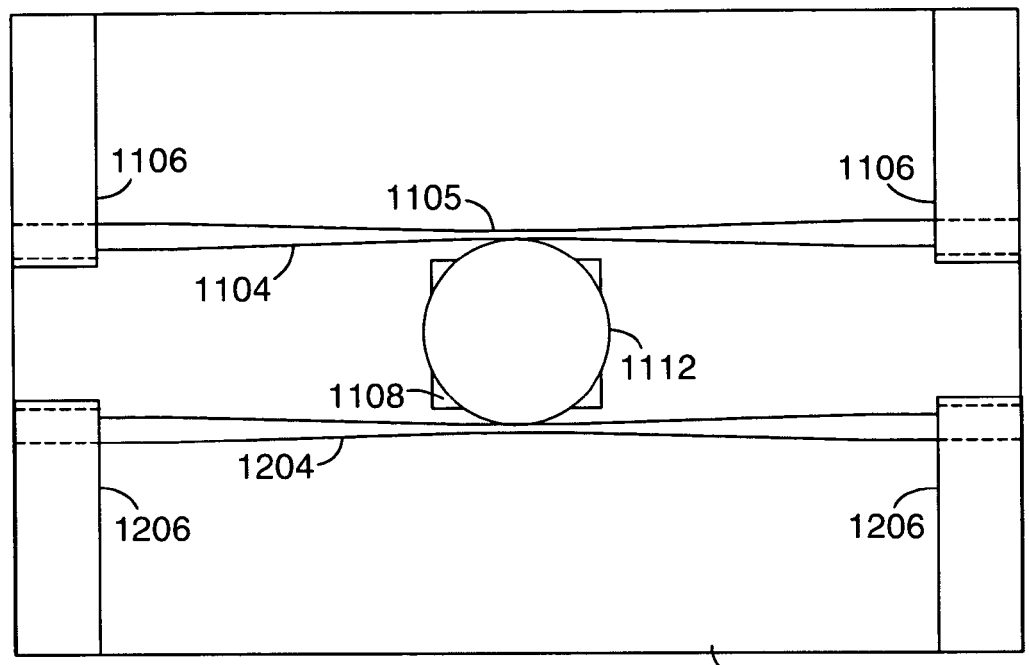
FIG. 12 schematically illustrates another embodiment of a microsphere resonator unit according to principles of the present invention.

Another embodiment is schematically illustrated in FIG. 12, in which a second fiber 1204, held between fiber holders 1206 is optically coupled to the microresonator 1112. This configuration permits light to be directed to the microresonator 1112 through one of the fibers 1104 and 1204, and for the light from the microresonator 1112 to propagate along the other fiber 1204 and 1104.

Alignment features may be formed on a substrate using several different approaches. One particular approach is to use a semiconductor substrate, for example a silicon substrate, and to use planar microfabrication techniques, such as lithography, masking and etching to form the device. For example, a groove or cavity may be etched in silicon. One approach to obtaining grooves or cavities with sloped surfaces is to perform a non-isotropic etch in a <100> silicon substrate: the vertex of the groove angle is about 70.5°, and is set by the crystalline geometry. Etching silicon in another crystalline direction may permit the fabrication of vertical walls. The width of an etched feature may controlled by a resist layer patterned on the surface of the substrate. In the case of a silicon substrate, the resist layer may be a silicon nitride layer. Thus, by proper masking and etching of the substrate, alignment features such as grooves, for example v-grooves or flat-bottomed grooves, may be formed. Also, the substrate surface may be formed with a hole, such as provided by a cavity, for locating a microresonator. Such lithographic techniques permit precise location of the features on the substrate, thus permitting passive alignment of the elements in the microresonator assembly. Waveguides may be formed in the silicon or in silicon oxide layers formed over the silicon substrate.

The term substrate as used here need not be restricted to only a single block of material that carries the microresonator, but should be understood to mean the support for the elements of the microresonator assembly. The substrate may be formed from more than one part. Also, the alignment features need not only be provided as parts etched into the upper surface of the substrate. An alignment feature may, for example, protrude from the surface on which the microresonator is resting, or the microresonator may itself may rest on the alignment features disposed with the substrate, for example as illustrated in the embodiment described with respect to FIG. 3A.

Figure 13:
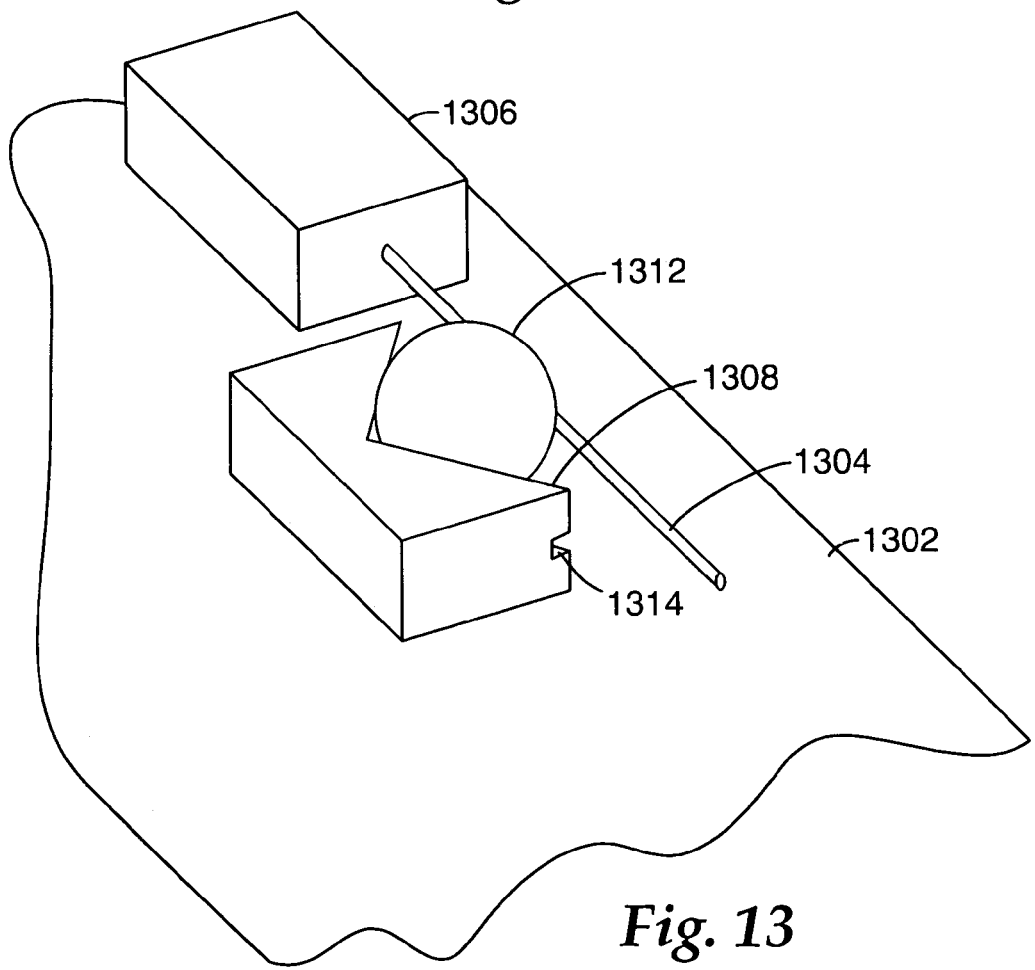
FIG. 13 schematically illustrates another embodiment of a microsphere resonator unit according to principles of the present invention.

Another example of this is schematically shown in FIG. 13, which shows a substrate 1302 having a self-aligning feature 1308 having a vertical groove to locate the microresonator 1312. A fiber waveguide 1304 may be held between fiber holders 1306 (only one of which is shown) so that there is good optical coupling between the fiber waveguide 1304 and the microresonator 1312. The groove walls may be shaped so as to reduce contact between the aligning element 1308 and the microresonator 1312 at the plane of light propagation within the microresonator 1312, for example with a relief groove 1314.

It will be appreciated that variations on the embodiments described herein still fall within the scope of the present invention. For example, the figures illustrate a microresonator that is circular or spherical in cross-section, although this need not be the case. The microresonator may be, for example, elliptical in cross-section. In such a case, the resonant optical path of the microresonator need not be circular, but may be non-circular. In addition, although only one microresonator has been shown to be retained on a substrate, it will be appreciated that multiple microresonators may be positioned on a single substrate, and may be coupled to a single waveguide or to different waveguides.

As noted above, the present invention is applicable to micro-resonators, and is believed to be particularly useful where micro-resonators are used in passive and active applications, such as sensing and laser applications. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A microresonator device, comprising:
a first substrate having at least one self-aligning feature on a surface;
a first waveguide disposed relative to the first substrate; and
a microresonator positioned on the substrate by the self-aligning feature so as to optically couple to the first waveguide in a coupling region, the first waveguide having a larger cladding index on the coupling region side than on an opposite side.

2. A device as recited in claim 1, wherein the self-aligning feature is a receiving cavity on the surface of the first substrate.

3. A device as recited in claim 1, wherein the self-aligning feature is a slot on the first substrate, wherein the microresonator is positioned at a location along the slot.

4. A device as recited in claim 3, wherein the first waveguide is positioned in the slot.

5. A device as recited in claim 3, wherein the microresonator contacts a slot edge, the slot edge being nonparallel with the first waveguide.

6. A device as recited in claim 3, wherein the microresonator contacts a slot edge, the slot edge being parallel with the first waveguide.

7. A device as recited in claim 3, wherein the slot has a first edge and a second edge closer to the first waveguide than the first edge, the microresonator being aligned by the first edge of the slot and the first waveguide.

8. A device as recited in claim 3, wherein the slot has a first edge and a second edge closer to the first waveguide than the first edge, the microresonator being aligned by the first edge of the slot and the second edge of the slot.

9. A device as recited in claim 1, wherein the first waveguide is disposed on the substrate, the first waveguide being unsupported by the substrate at a coupling region of the waveguide.

10. A device as recited in claim 1, wherein a direction of optical coupling between the first waveguide and the microresonator is parallel to the surface of the first substrate.

11. A device as recited in claim 1, wherein a direction of optical coupling between the first waveguide and the microresonator is perpendicular to the surface of the first substrate.

12. A device as recited in claim 1, wherein the first waveguide is an optical fiber.

13. A device as recited in claim 12, wherein the optical fiber is a tapered optical fiber.

14. A device as recited in claim 1, wherein the first waveguide is a planar waveguide.

15. A device as recited in claim 1, wherein the first waveguide is a channel waveguide.

16. A device as recited in claim 1, wherein the microresonator is microsphere.

17. A device as recited in claim 1, further comprising an adhesive material disposed to hold the microresonator to the self-aligning feature.

18. A device as recited in claim 1, further comprising at least one retaining member disposed to retain the microresonator at a desired location relative to the self-aligning feature.

19. A device as recited in claim 1, further comprising a second substrate and a second waveguide disposed relative to the second substrate, the second waveguide being optically coupled to the microresonator.

20. A device as recited in claim 1, further comprising a light source generating light, the light being coupled to the first waveguide and from the first waveguide to the microresonator.

21. A device as recited in claim 20, further comprising a light detector optically coupled to detect light from the microresonator.

22. A device as recited in claim 20, wherein the light detector is coupled to receive light from the microresonator via the first waveguide.

23. A device as recited in claim 1, wherein the microresonator further comprises an optical gain medium.

24. A device as recited in claim 1, further comprising a second waveguide disposed relative to the first substrate, the second waveguide being optically coupled to the first microresonator.

25. A device as recited in claim 1, further comprising a second substrate disposed proximate the first substrate.

26. A device as recited in claim 25, further comprising a second waveguide disposed relative to one of the first and second substrates, the second waveguide being optically coupled to the first microresonator.

27. A device as recited in claim 26, wherein the first waveguide is attached to the first substrate and the second waveguide is attached to the second substrate.

28. A method of making a microresonator optical device, comprising:
providing at least one self-aligning feature on a first substrate;
providing a first waveguide; and
positioning a microresonator, using the at least one self-aligning feature, so that the microresonator is in an optically coupling relationship with the first waveguide in a coupling region, the first waveguide having a larger cladding index on the coupling region side than on an opposite side.

29. A method as recited in claim 28, wherein providing the at least one self-aligning feature on the first substrate comprises forming a receiving cavity on a surface of the substrate and positioning the microresonator comprises positioning the microresonator in the cavity.

30. A method as recited in claim 28, wherein providing the at least one self-aligning feature on the first substrate comprises forming a slot on a surface of the first substrate.

31. A method as recited in claim 30, wherein providing the first waveguide comprises providing the first waveguide in the slot.

32. A method as recited in claim 30, wherein forming the slot comprises forming a slot edge non-parallel with the first waveguide.

33. A method as recited in claim 28, wherein providing the at least one self-aligning feature comprises etching the at least one self-aligning feature in a surface of the substrate.

34. A method as recited in claim 28, further comprising optically coupling light between the first waveguide and the microresonator in a direction parallel to a major surface of the substrate.

35. A method as recited in claim 28, further comprising optically coupling light between the first waveguide and the microresonator in a direction perpendicular to a major surface of the substrate.

36. A method as recited in claim 28, further comprising adhering the microresonator to the first substrate to hold the microresonator in a fixed relationship relative to the self-aligning structure.

37. A method as recited in claim 28, further comprising fixing the microresonator at a desired location relative to the self-aligning element with at least one retaining member.

38. A method as recited in claim 28, further comprising providing a second substrate and a second waveguide disposed relative to the second substrate, and optically coupling light between the microresonator and the second waveguide.

* * * * *

UNITED STATES PATENT AND TRADEMARK OFFICE
CERTIFICATE OF CORRECTION

PATENT NO. : 7,444,045 B2  
APPLICATION NO. : 10/685049  
DATED : October 28, 2008  
INVENTOR(S) : Xudong Fan Page 1 of 1

It is certified that error appears in the above-identified patent and that said Letters Patent is hereby corrected as shown below:

<u>Title Page, Item (56) Page 2,</u>  
Under Other Publications, line 8, 1st Burlak, et al. delete "Osciliations" and insert -- Oscillations --.

<u>Column 5,</u>  
Line 19, delete "maybe" and insert -- may be --.

<u>Column 11,</u>  
Lines 63 and 64, in Claim 20, delete "microresonatOr." and insert -- microresonator. --.

Signed and Sealed this

Third Day of March, 2009

JOHN DOLL  
*Acting Director of the United States Patent and Trademark Office*